US007943398B2

(12) United States Patent
Park

(10) Patent No.: US 7,943,398 B2
(45) Date of Patent: May 17, 2011

(54) RESONANT MAGNETIC DISKS FOR BIOANALYTE DETECTION

(75) Inventor: Chang-Min Park, Portland, OR (US)

(73) Assignee: Intel Corporation, Santa Clara, CA (US)

(*) Notice: Subject to any disclaimer, the term of this patent is extended or adjusted under 35 U.S.C. 154(b) by 550 days.

(21) Appl. No.: 11/771,833

(22) Filed: Jun. 29, 2007

(65) Prior Publication Data

US 2009/0004758 A1 Jan. 1, 2009

(51) Int. Cl.
*G01N 33/543* (2006.01)
*G01N 33/53* (2006.01)

(52) U.S. Cl. .................. 436/526; 436/518; 435/7.1

(58) Field of Classification Search .............. 436/526, 436/518; 435/7.1
See application file for complete search history.

(56) References Cited

U.S. PATENT DOCUMENTS

| 4,444,879 | A | * | 4/1984 | Foster et al. | ............ 435/7.95 |
| 6,107,102 | A | * | 8/2000 | Ferrari | ............ 436/518 |
| 6,790,378 | B2 | * | 9/2004 | Graham et al. | ............ 252/62.53 |
| 2002/0137059 | A1 | * | 9/2002 | Wu et al. | ............ 435/6 |

OTHER PUBLICATIONS

V. Novosad et al., Magnetic Vortex Resonance in Patterned Ferromagnetic Dots, Materials Science Division and Center for Nanoscale Materials, Argonne National Laboratory, Argonne, IL, Mar. 18, 2005, pp. 1-17.

* cited by examiner

*Primary Examiner* — Mark L Shibuya
*Assistant Examiner* — Pensee T Do
(74) *Attorney, Agent, or Firm* — Pillsbury Winthrop Shaw Pittman LLP

(57) ABSTRACT

Embodiments of the invention relate generally to ferromagnetic microdisks, methods of detecting target bioanalyte using ferromagnetic microdisks, and kits (such as for using in the laboratory setting) containing the reagents necessary to make, and/or use ferromagnetic microdisks for bioanalyte detection, depending on the user's planned application. The methods and products allow the fabrication of ferromagnetic microdisks, and their use in the detection of biological molecules with high sensitivity, little or no signal decay, improved safety, convenience, and lowered cost for use and disposal.

31 Claims, 3 Drawing Sheets

RESONANT MAGNETIC DISKS FOR BIOANALYTE DETECTION

FIELD OF INVENTION

Embodiments of the invention relate to ferromagnetic microdisks bioconjugated to molecular probes, and methods of using bioconjugated ferromagnetic microdisks for detecting biological molecules (bioanalytes).

BACKGROUND

The ability to detect and identify trace quantities of analytes has become increasingly important in virtually every scientific discipline, ranging from part per billion analyses of pollutants in sub-surface water to analysis of cancer treatment drugs in blood serum.

With the advancement of technologies to make and detect biomolecules, there are multiple techniques that promise biological detection with single molecule sensitivity. However, many of these techniques have not yet found commercial applications or feasibility. The main reasons are the complexity associated with these ultra-sensitive methods, the costs, and the potential biohazards associated with the reagents. Many methods require multiple steps of chemical treatments, bulky and expensive instruments, and/or extreme care in sample handling and observation. These are not ideal for practical applications that require easy and reliable measurements that are flexible enough for user's needs.

Additionally, many of the currently used methods of detecting bioanalytes rely on markers or "tags" that bind to the bioanalytes and are detected, thereby indirectly detecting the bioanalytes(s) of interest. However, the markers or tags such as radioisotope-labeled probes, or fluorescent markers, can lose their signal intensity over time. For example, radioisotopes commonly used as "tags" or "markers" decay over time, causing a gradual loss of signal that can be detected. Because of this, some experiments need to be conducted rapidly before the signal decays beyond the limits of detection. Similarly, fluorescent probes are subject to "photobleaching" wherein exposure to ambient light causes the fluorescent probe to bleach or fade away. Again, often experiments need to be conducted quickly before photobleaching occurs, or inconveniently in a dark setting so as to avoid photobleaching.

Safety is another consideration. Radioactive labels and their required reagents must be used in carefully monitored situations due to their known biologic hazards. Radioactive wastes produced from common detection methods must be carefully disposed of so as to avoid environmental contamination. Similarly, the toxicity of cadmium in quantum dots and relatively large size of dye-loaded particles have limited their applications. Although very small size (down to 10 nm in diameter) detection has been achieved for conjugated polymer particles, their signal intensity is lower than the larger fluorescent particles. Lower signal intensity makes the particles more difficult to detect with conventional techniques.

Finally, the cost of radioactive and fluorescent substances can be substantial, both in terms of acquisition, use, safety monitoring, and their proper monitoring and disposal.

Accordingly, there is a need for a reagents methods of bioanalyte detection wherein the marker to be detected exhibits little or no signal decay, and can be safely utilized in a variety of environments without posing risks to the user or to the environment. Preferably, a marker would have a high safety profile, exhibit a long (non or low-decaying) signal intensity, and be available to users at a low cost for reagent use and disposal.

DETAILED DESCRIPTION

Figure 1:
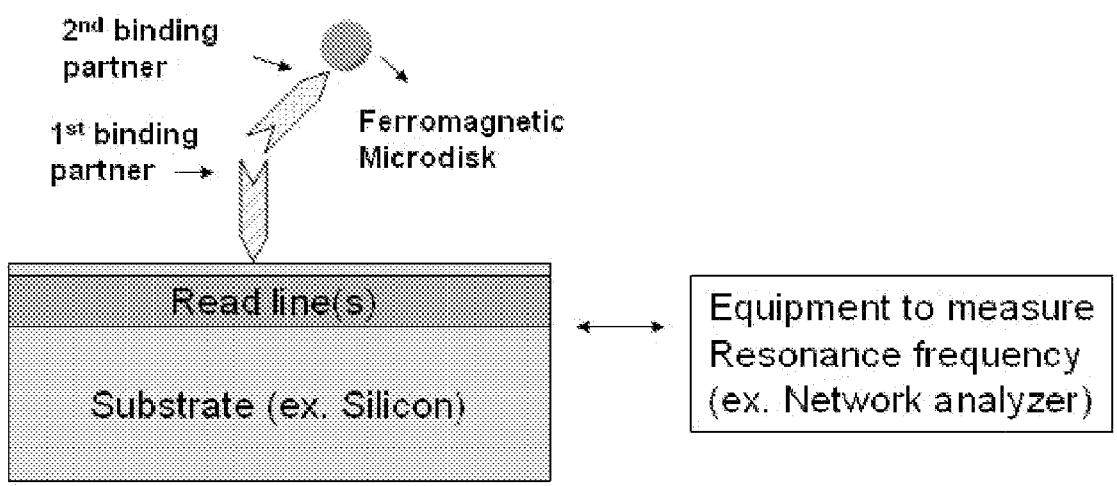
FIG. 1 is a cross-sectional schematic illustrating skeleton components of tag-based detection of biomolecules (bioanalytes) using magnetic vortex resonance labeling and detection.

Embodiments of the invention relate to ferromagnetic microdisks bioconjugated to molecular probes, and methods of using bioconjugated ferromagnetic microdisks for detecting biological molecules (bioanalytes) with high sensitivity and improved ease of use and safety profiles. The embodiments are especially directed to making and utilizing conjugated ferromagnetic microdisks that exhibit a unique resonance frequency depending on the geometry of the ferromagnetic microdisk, in which the resonance frequency can be detected by appropriate instruments for the detection of one or more bioanalyte of interest. Because the resonance frequency exhibited by the ferromagnetic microdisk is a magnetic signal, it does not decay or diminish over time. The invention transcends several scientific disciplines such as polymer chemistry, biochemistry, molecular biology, medicine, and medical diagnostics.

As used in the specification and claims, the singular forms "a," "an," and "the" include plural references unless the context clearly dictates otherwise. For example, the term "an array" may include a plurality of arrays unless the context clearly dictates otherwise.

A "ferromagnetic microdisk" is one or more of an intentionally created devices that can be prepared by a variety of methods known in the art, such as photolithography. The ferromagnetic microdisks exhibit (i.e., emit) a unique magnetic vortex resonance depending on the geometry of the microdisk, such as the diameter and thickness of the microdisk. Ferromagnetic microdisks can be attached (bioconjugated) to chosen molecular probes that are specific to various bioanalytes of interest. The unique vortex resonance exhibited by the ferromagnetic microdisk can be detected using common apparatus in the art.

The terms "nanomaterial" and "nanoparticle" as used herein refer to a structure, a device, or a system having a dimension at the atomic, molecular or macromolecular levels, in the length scale of approximately 1-1000 nanometer range, preferably in the range of about 2 m to about 200 mm, more preferably in the range of about 2 nm to about 50 nm.

The term "bioanalyte," "analyte," "target," or "target molecule" refers to a molecule of interest in a sample that is to be detected, analyzed, and/or quantified in some manner. Examples of bioanalytes include, but are not limited to, amino acids, peptides, polypeptides, proteins, glycoproteins, lipoproteins, nucleosides, nucleotides, oligonucleotides, nucleic acids, sugars, carbohydrates, oligosaccharides, polysaccharides, fatty acids, lipid, hormones, metabolites, cytokines, chemokines, receptors, neurotransmitters, antigens, allergens, antibody, substrates, metabolites, cofactors, inhibitors, drugs, pharmaceuticals, nutrients, prions, toxins, poisons, explosives, pesticides, chemical warfare agents, biohazardous agents, radioisotopes, vitamins, heterocyclic aromatic compounds, carcinogens, mutagens, narcotics, amphetamines, barbiturates, hallucinogens, and waste products and/or contaminants. In certain embodiments of the invention, one or more bioanalytes may be contacted with, and joined to such as by hybridization, one or more biomolecular probes, as disclosed below, which are themselves bound to ferromagnetic microdisks.

The sample such as a bioanalyte in the embodiments of this invention can be in the form of solid, liquid or gas, or solution. The sample can be analyzed by the embodiments of the methods and devices of this invention when the sample is at room temperature, and at lower than or higher than the room temperature. Samples may be obtained from any source, biologic or non-biologic.

Further, the bioanalyte could be an organic or inorganic molecule. Some examples of analytes may include a small molecule, a biomolecule, or a nanomaterial such as but not necessarily limited to a small molecule that is biologically active, nucleic acids and their sequences, peptides and polypeptides, as well as nanostructure materials chemically modified with biomolecules or small molecules capable of binding to molecular probes such as chemically modified carbon nanotubes, carbon nanotube bundles, nanowires, nanoclusters or nanoparticles. The bioanalyte molecule may be a fluorescently labeled molecule, such as DNA or RNA.

The term "fluid" used herein means an aggregate of matter that has the tendency to assume the shape of its container, for example a liquid or gas. Analytes in fluid form can include fluid suspensions and solutions of solid particle analytes.

The term "bi-functional linker group" refers to an organic chemical compound that has at least two chemical groups or moieties, such as for example, carboxyl group, amine group, thiol group, aldehyde group, epoxy group, that can be covalently modified specifically; the distance between these groups is equal to or greater than 5-carbon bonds.

The term "molecular probe," "biomolecular probe," "capture molecule," or "affinity agent" refers to a molecule or group/collection of molecules that is attached ("bioconjugated"), reversibly or irreversibly, to a ferromagnetic microdisk. The molecular probe generally, but not necessarily, also binds to one or more bioanalytes of interest, as described above. The biomolecular probe is typically a nucleotide, an oligonucleotide, or a protein, but can also be a small molecule, biomolecule, or nanomaterial such as, but not necessarily limited to, a small molecule that is biologically active, nucleic acids and their sequences, peptides and polypeptides, as well as nanostructure materials chemically modified with biomolecules or small molecules capable of binding to a target molecule that is bound to a probe molecule to form a complex of the capture molecule, target molecule and the probe molecule. The capture molecule may be fluorescently labeled DNA or RNA. The capture molecule may or may not be capable of binding to just the target bioanalyte or just the probe molecule. Other molecular probes include, for example, antibodies, antibody fragments, antigens, epitopes, lectins, proteins, polypeptides, receptor proteins, ligands, hormones, vitamins, metabolites, substrates, inhibitors, cofactors, pharmaceuticals, aptamers, cytokines and neurotransmitters.

The term "molecule" generally refers to a macromolecule or polymer as described herein. However, SEF nanoparticles comprising single molecules, as opposed to macromolecules or polymers, are also within the scope of the embodiments of the invention.

A "macromolecule" or "polymer" comprises two or more monomers covalently joined. The monomers may be joined one at a time or in strings of multiple monomers, ordinarily known as "oligomers." Thus, for example, one monomer and a string of five monomers may be joined to form a macromolecule (polymer) of six monomers. Similarly, a string of fifty monomers may be joined with a string of hundred monomers to form a macromolecule or polymer of one hundred and fifty monomers. The term polymer as used herein includes, for example, both linear and cyclic polymers of nucleic acids, polynucleotides, polynucleotides, polysaccharides, oligosaccharides, proteins, polypeptides, peptides, phospholipids and peptide nucleic acids (PNAs). The peptides include those peptides having either $\alpha$-, $\beta$-, or $\omega$-amino acids. In addition, polymers include heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure.

The term "nucleotide" includes deoxynucleotides and analogs thereof. These analogs are those molecules having some structural features in common with a naturally occurring nucleotide such that when incorporated into a polynucleotide sequence, they allow hybridization with a complementary polynucleotide in solution. Typically, these analogs are derived from naturally occurring nucleotides by replacing and/or modifying the base, the ribose or the phosphodiester moiety. The changes can be tailor-made to stabilize or destabilize hybrid formation, or to enhance the specificity of hybridization with a complementary polynucleotide sequence as desired, or to enhance stability of the polynucleotide.

The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (cDNA) which may be isolated from natural sources, recombinantly produced, or artificially synthesized. A further example of a polynucleotide of the embodiments of the invention may be polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as "nucleotide polymers.

An "oligonucleotide" is a polynucleotide having 2 to 20 nucleotides. Analogs also include protected and/or modified monomers as are conventionally used in polynucleotide synthesis. As one of skill in the art is well aware, polynucleotide synthesis uses a variety of base-protected nucleoside derivatives in which one or more of the nitrogens of the purine and pyrimidine moiety are protected by groups such as dimethoxytrityl, benzyl, tert-butyl, isobutyl and the like.

For instance, structural groups are optionally added to the ribose or base of a nucleoside for incorporation into a polynucleotide, such as a methyl, propyl or allyl group at the 2'-O position on the ribose, or a fluoro group which substitutes for the 2'-O group, or a bromo group on the ribonucleoside base. 2'-O-methyloligoribonucleotides (2'-O-MeORNs) have a higher affinity for complementary polynucleotides (especially RNA) than their unmodified counterparts. Alternatively, deazapurines and deazapyrimidines in which one or more N atoms of the purine or pyrimidine heterocyclic ring are replaced by C atoms can also be used.

The phosphodiester linkage, or "sugar-phosphate backbone" of the polynucleotide can also be substituted or modified, for instance with methyl phosphonates, O-methyl phosphates or phosphorothioates. Another example of a polynucleotide comprising such modified linkages for purposes of this disclosure includes "peptide polynucleotides" in which a polyamide backbone is attached to polynucleotide bases, or modified polynucleotide bases. Peptide polynucleotides which comprise a polyamide backbone and the bases found in naturally occurring nucleotides are commercially available.

When the macromolecule of interest is a peptide, the amino acids can be any amino acids, including $\alpha$, $\beta$, or $\omega$-amino acids. When the amino acids are a-amino acids, either the L-optical isomer or the D-optical isomer may be used. Additionally, unnatural amino acids, for example, $\beta$-alanine, phenylglycine and homoarginine are also contemplated by the embodiments of the invention. These amino acids are well-known in the art.

A "peptide" is a polymer in which the monomers are amino acids and which are joined together through amide bonds and alternatively referred to as a polypeptide. In the context of this specification it should be appreciated that the amino acids may be the L-optical isomer or the D-optical isomer. Peptides are two or more amino acid monomers long, and often more than 20 amino acid monomers long.

A "protein" is a long polymer of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples of proteins include hormones, enzymes, and antibodies.

The term "sequence" refers to the particular ordering of monomers within a macromolecule and it may be referred to herein as the sequence of the macromolecule.

A "ligand" is a molecule that is recognized by a particular receptor. Examples of ligands that can be investigated by this invention include, but are not restricted to, agonists and antagonists for cell membrane receptors, toxins and venoms, viral epitopes, hormones, hormone receptors, peptides, enzymes, enzyme substrates, cofactors, drugs (e.g. opiates, steroids, etc.), lectins, sugars, polynucleotides, nucleic acids, oligosaccharides, proteins, and monoclonal antibodies.

A "receptor" is molecule that has an affinity for a given ligand. Receptors may-be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term "receptors" is used herein, no difference in meaning is intended. A "Ligand Receptor Pair" is formed when two macromolecules have combined through molecular recognition to form a complex. Other examples of receptors which can be investigated by this invention include but are not restricted to:

a) Microorganism receptors: Determination of ligands which bind to receptors, such as specific transport proteins or enzymes essential to survival of microorganisms, is useful in developing a new class of antibiotics. Of particular value would be antibiotics against opportunistic fungi, protozoa, and those bacteria resistant to the antibiotics in current use.

b) Enzymes: For instance, one type of receptor is the binding site of enzymes such as the enzymes responsible for cleaving neurotransmitters; determination of ligands which bind to certain receptors to modulate the action of the enzymes which cleave the different neurotransmitters is useful in the development of drugs which can be used in the treatment of disorders of neurotransmission.

c) Antibodies (Abs): For instance, the invention may be useful in investigating the ligand-binding site on the antibody molecule which combines with the epitope of an antigen of interest; determining a sequence that mimics an antigenic epitope may lead to the-development of vaccines of which the immunogen is based on one or more of such sequences or lead to the development of related diagnostic agents or compounds useful in therapeutic treatments such as for auto-immune diseases (e.g., by blocking the binding of the "anti-self" antibodies). There are monoclonal antibodies (mAb) and polyclonal antibodies (pAb).

d) Nucleic Acids: Sequences of nucleic acids may be synthesized to establish DNA or RNA binding sequences. Certain sequence of nucleic acids, called aptamer, can bind to proteins or peptides.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant.

f) Hormone receptors: Examples of hormones receptors include, e.g., the receptors for insulin and growth hormone. Determination of the ligands which bind with high affinity to a receptor is useful in the development of, for example, an oral replacement of the daily injections which diabetics take to relieve the symptoms of diabetes. Other examples are the vasoconstrictive hormone receptors; determination of those ligands which bind to a receptor may lead to the development of drugs to control blood pressure.

g) Opiate receptors: Determination of ligands which bind to the opiate receptors in the brain is useful in the development of less-addictive replacements for morphine and related drugs.

A "linker" molecule refers to any of those molecules described supra, such as for example molecular probes, and preferably should be about 4 to about 100 atoms long to provide sufficient exposure. The linker molecules may be, for example, aryl acetylene, alkane derivatives, ethylene glycol oligomers containing 2-10 monomer units, diamines, diacids, amino acids, among others, and combinations thereof. Alternatively, the linkers may be the same molecule type as that being synthesized (i.e., nascent polymers), such as polynucleotides, oligopeptides, or oligosaccharides.

The term "fluid" used herein means an aggregate of matter that has the tendency to assume the shape of its container, for example a liquid or gas. Analytes in fluid form can include fluid suspensions and solutions of solid particle analytes.

The term "attached," as in, for example, the "attachment" of a molecular probe to a ferromagnetic microdisk, includes covalent binding, adsorption, and physical immobilization. The terms "associated with," "binding," and "bound" are identical in meaning to the term "attached." Attachment of molecular probe to ferromagnetic microdisk, or molecular probe to bioanalyte, can be permanent or reversible.

The term "permalloy" refers to a nickel iron magnetic alloy. Generically, it refers to an alloy with about 20% iron and 80% nickel content (i.e., Ni80Fe20). Permalloy has a high magnetic permeability, low coercivity, near zero magnetostriction, and significant anisotropic magnetoresistance. This alloy is used, for example, in transformer laminations and magnetic recording head sensors. Permalloy's electrical resistivity generally varies within the range of 5% depending on the strength of the magnetic field. The low magnetostriction is helpful for industrial applications, where variable stresses in thin films would otherwise cause a ruinously large variation in magnetic properties. Other compositions of permalloy are available, designated by a numerical prefix denoting the percentage of nickel in the alloy, for example 45 permalloy containing 45% nickel, and 55% iron. Molybdenum permalloy is an alloy of 81% nickel, 17% iron and 2% molybdenum.

Other ferromagnetic materials are encompassed by embodiments of the invention. For example, ferromagnetic microdisks can be fabricated with substances such as CoNiFe, CoFe, CoFeCu, CoZrTa, and other ferromagnetic metals or alloys.

Embodiments of the invention relate generally to ferromagnetic microdisks bound to molecular probe, methods of detecting target bioanalyte using ferromagnetic microdisks, and kits (such as for using in the laboratory setting) containing the reagents necessary to make, and/or use ferromagnetic microdisks for bioanalyte detection, depending on the user's planned application. The methods and products allow the fabrication of ferromagnetic microdisk/molecular probe complexes, and their use in the detection of biological molecules (bioanalytes) with high sensitivity, little or no signal decay, improved safety, convenience, and lowered cost of use and disposal. The embodiments are especially directed to utilizing ferromagnetic microdisks exhibiting unique resonance frequency as "tags," and identifying the tags using detection of the unique resonance frequency by known means, or other detection methods wherein ferromagnetic microdisks can be detected and/or observed. Ferromagnetic microdisks can be used in solution or attached to a substrate for bioanalyte detection, depending on user needs.

One embodiment is a ferromagnetic microdisk, constructed from a ferromagnetic material, that exhibits a unique resonance frequency determined by the geometry of the microdisk, and a molecular probe attached to the ferromagnetic microdisk. Preferably, the ferromagnetic material is permalloy.

Preferably, ferromagnetic microdisks have a diameter of less than about 3 µm and a thickness of less than about 50 nm. More preferably, ferromagnetic microdisks have a diameter of about 1.1 µm to about 2.2 µm, and a thickness of about 20 nm to about 40 nm.

Preferably, ferromagnetic microdisks are fabricated, and the geometry is determined, by photolithography.

In embodiments of the invention, the ferromagnetic microdisks exhibit a unique resonance frequency ranging from about 25 mHz to about 400 mHz. Preferably, the unique resonance frequency is from about 80 to about 272. mHz. More preferably, the resonance frequency is about 83, 162, or 272 mHz.

Preferably, ferromagnetic microdisks of the invention are attached to molecular probes. Molecular probes include, for example, antibody, antigen, ligand, receptor, aptamer, or a nucleic acid. More preferably, the molecular probe comprises an antibody or a nucleic acid. More preferably, the molecular probe attached to the ferromagnetic disk comprises protein.

Another embodiment is a method of detecting a target bioanalyte, such as a biomolecule of interest, with a ferromagnetic microdisk by attaching ("bioconjugating") one or more molecular probes to one or more ferromagnetic microdisks that are made of a ferromagnetic material and exhibit a unique resonance frequency; contacting the bioconjugated ferromagnetic microdisk with at least one target bioanalyte of interest; binding the molecular probe to the target analyte, and detecting the unique resonance frequency exhibited by the ferromagnetic microdisk, thereby detecting presence of the ferromagnetic microdisk and thus the presence of at least one target bioanalyte which has bound to the molecular probe on the ferromagnetic microdisk.

Preferably, the molecular probe attached to the ferromagnetic disk is chosen from an antibody, antigen, ligand, receptor, aptamer, and nucleic acid. More preferably, the molecular probe comprises protein.

In one embodiment of the invention, the target bioanalyte is present in a solid sample. In another embodiment, the target bioanalyte is present in a solution. In certain embodiments, the target bioanalyte is bound to a solid or semisolid support or matrix.

Preferably, the target bioanalyte is present in vitro. More preferably, the target bioanalyte is present in vivo.

In other embodiments of the invention, the bioanalyte to be detected is present in a non-living sample, such as for example, a food sample, soil sample, or water sample. Embodiments of the invention are not limited to biological samples or tissues, and can be used in industry, geology, an contamination detection.

Another embodiment of the invention is a kit that includes one or more ferromagnetic microdisks and one or more molecular probes attached to the ferromagnetic microdisk, wherein the ferromagnetic microdisks comprise a ferromagnetic material and exhibit a unique resonance frequency determined by the geometry of the microdisk.

Preferably, the ferromagnetic microdisks comprise permalloy film.

Preferably, the molecular probe is selected from the group consisting of antibody, antigen, ligand, receptor, aptamer, and nucleic acid. More preferably, the molecular probe comprises protein.

Embodiments of the invention encompass ferromagnetic microdisks that include a ferromagnetic material and exhibit a unique resonance frequency determined by the geometry of the microdisk. The manufacture and resonance frequency characteristics of ferromagnetic microdisks have been described in the art (see Novosad, et al., Magnetic Vortex Resonance in Patterned Ferromagnetic Dots, *Physical Review*, B72, 024455-1-5 (2005), the entire disclosure of which is hereby incorporated by reference).

Embodiments of this invention addresses the problem of:
(1) target bioanalyte detection when present in low levels in the target sample; (2) highly sensitive detection of antigens, antibodies, and viruses, and other bioanalytes; (3) using markers or tags that are safe to the use and environmentally sound, are easy to use, and that exhibit a signal that does not decay or degrade over time or with use. As a result, embodiments of the invention simplify sample preparation and significantly lower the costs and biohazards associated with bioanalyte detection.

As described, embodiments of this invention provide highly sensitive devices and methods for bioanalyte detection. With a biomolecular probe attached to ferromagnetic microdisk, mass sensitivity can be estimated as follows. Note that each spectrum shown in FIG. 3 was collected from ~1200 microdisks. Mass of biomolecule is ~1000 kDa (kilo Dalton. 1 Da~$1.66 \times 10^{-27}$ kg). As examples, the mass of yeast protein and titins protein is 53 kDa and 3000 kDa, respectively. The mass sensitivity can be calculated as follows.

$$1200 \text{ biomolecules} \times 1000 \text{ kDa} = 1,200,000 \text{ kDa} \sim 2 \times 10^{-18} \text{ kg}.$$

The mass sensitivity is therefore $\sim 10^{-18}$ kg.

In the embodiments of the invention, permalloy films are preferred substrate for ferromagnetic microdisks. Such films have been shown to be useful for the fabrication of ferromagnetic microdisks. However, other ferromagnetic materials can be used, such as for example CoNiFe, CoFe, CoFeCu, CoZrTa, and other ferromagnetic metals or alloys.

Some of the technical advantages of the embodiments of the invention include the following:
(1) Target bioanalytes (e.g., proteins or nucleic acids) need not be labeled or amplified (DNA). This is because ferromagnetic microdisk detection is a label-free strategy that is superior to fluorescence technology in which target samples must be labeled with fluorescent molecules that are prone to photobleaching. Thus, tedious, error-prone, costly, and environmentally unfriendly (e.g., radioisotope labeling) sample preparation steps can be avoided.
(2) Multiple targets can be detected at the same time in one sample by using multiple ferromagnetic microdisks variable bioconjugated molecular probes. Ferromagnetic microdisks can be "free" in a sample, or alternatively, bound to a solid or semisolid substrate, such as for example, an array, wherein a test sample is applied to the array and for bioanalyte detection with complementary molecular probes. Ferromagnetic microdisks can be used in discrete units, i.e., ferromagnetic microdisks with one type of molecular probe that is specific to one particular bioanalyte, or alternatively, ferromagnetic microdisks can be used with a library of molecular probes that are specific to a myriad of bioanalytes. This latter embodiment is advantageous in the fabrication and use of ferromagnetic microdisks in an array.
(3) Each bioanalyte molecule detection can be verified by duplication using the same detection probe but with a different ferromagnetic microdisk. The multiplicity of ferromagnetic microdisk detection allows redundant measurement, thereby providing greater control increased credibility of the test results.
(4) The structure of ferromagnetic microdisks and their respective attached biomolecular probes can be easily finetuned to meet specific applications in diagnostics and drug discovery.

Embodiments of this invention have several useful applications. For example, ferromagnetic microdisks can be employed for the ultra-sensitive detection of bioanalytes including, antibodies, antigens, biomarkers, allergens, ligands, metabolites, virus, bacteria, tumor cells, etc. The ability to detect, locate, and/or quantify bioanalytes allows for diagnostic use, treatment, and/or monitoring of specific diseases, physiological conditions (normal or abnormal), conditions, and therapies. For example, detection of abnormal proteins in human disease could detected. As another example, the normal signal transduction inside, or outside cells could be detected and monitored. It is envisioned that embodiments of the invention could be used in vivo or in vitro for screening purposes, i.e., high throughput methods of evaluating pathological conditions. High-throughput drug discovery screening is another example where embodiments of the invention would be useful.

Resonance frequency detection, for example with equipment to measure resonance frequency such as a network analyzer could be employed in both normal physiological systems (e.g., at the cellular, tissue, and whole animal level), and also in pathological states for disease evaluation. Embodiments of the invention are also useful in flow cytometry, environmental monitoring, and food analysis.

In order to provide users with the ability to efficiently utilize embodiments of the invention, the present invention contemplates methods and kits for screening samples containing suspected analytes of interest that could be detected with ferromagnetic microdisks. The kits contain the reagents necessary to manufacture ferromagnetic microdisks, including the disks, reagents for attaching one or more molecular probe(s) that can bind to the target bioanalyte of interest. Such kits are advantageous for users who want to create ferromagnetic microdisks and attach molecular probes that will be useful in specific applications, such as for example, locating, quantifying, and or analyzing particular target bioanalytes of interest.

For example, one kit contains all the reagents necessary for the production of ferromagnetic microdisks, and a molecular probe, such as a particular receptor, that is conjugated to the ferromagnetic microdisks; in this manner, the ferromagnetic microdisk has been "tagged" with a molecular probe. The particular receptor, when contacted to a sample of interest, will bind to a cellular protein (bioanalyte) of interest that is specific for, or complementary to, the molecular probe attached to the ferromagnetic microdisk. The target sample containing bioanalyte can be derived from, for example, a cell culture (i.e., in vitro), or from a mammalian sample (i.e., in vivo). After contacting the tagged ferromagnetic microdisk with bioanalyte of interest, the ferromagnetic microdisk is detected based on its unique resonance frequency (using, for example, detectors that recognize the characteristic magnetic vortex resonance frequency emitted by the ferromagnetic microdisk), thereby detecting the presence (or absence), quantity, and location of the target cellular protein (i.e., bioanalyte) of interest. This example is merely illustrative, and not intended to be limiting.

Although embodiments have been described in which small molecules and proteins are described as being the analytes, it is understood, however, that the same process and tools can be used to detect the binding of a variety of analytes to one another and the invention is not limited to just the binding of small molecules to proteins.

Example 1

FIG. 1 shows an exemplary ferromagnetic microdisk that is attached to a molecular probe ("linker") which acts as a binding partner to a bioanalyte of interest. The ferromagnetic microdisk is made of a ferromagnetic material, such as permalloy, that is well known in the art. Ferromagnetic microdisks exhibit a unique resonance frequency based on their geometry, such as the diameter and thickness of the microdisk; by altering the geometric parameters, ferromagnetic microdisk are made with specific unique resonance frequencies.

As shown in FIG. 1, tagged biomolecule(s) approach the read line (which are simply conducting lines such as copper), the ferromagnetic microdisk is detected by evaluating the characteristic magnetic vortex resonance frequency. Read lines may be microwave coplanar waveguides used to generate magnetic field and collect (i.e., detect) the frequency spectrum. Microchannel may be formed in order to provide closed volume within which all biomolecules and ferromagnetic microdisks can be confined.

The ferromagnetic microdisk, preferably the outer surface thereof, is bioconjugated to a molecular probe and the complex is used for bioanalyte detection. The ferromagnetic microdisks are functionalized with an molecular probe, such as an amine group. Various bioanalytes of interest in a sample are contacted with, and conjugated to, the functionalized ferromagnetic microdisks through bioconjugation methods for that are well known in the art, such as hybridization. Bioanalytes of interest to be detected include, for example, proteins, antibodies, enzymes, nucleic acids (DNA, RNA, oligonucleotides), antigen, peptides, ligands, receptors, small molecules, metabolites, etc. Although the biological applications of the bioconjugated ferromagnetic microdisk is are immense, detection of signature antibody, autoantibody, antigen, virus and bacterium are of special interest for disease diagnostics and treatment monitoring.

The bioanalyte of interest is now bound to one or more ferromagnetic microdisks because the molecular probe (conjugated to the surface of the ferromagnetic microdisk) also binds to the bioanalyte of interest. The bionanlyte of interest is now located and quantified by detection of the unique resonance frequency emitted by the bound ferromagnetic microdisk. The resonance frequency is detected with a magnetic signal detector and network analyzer; such methods that are well known in the art for detecting and quantify magnetic signals.

Example 2

Figure 2:
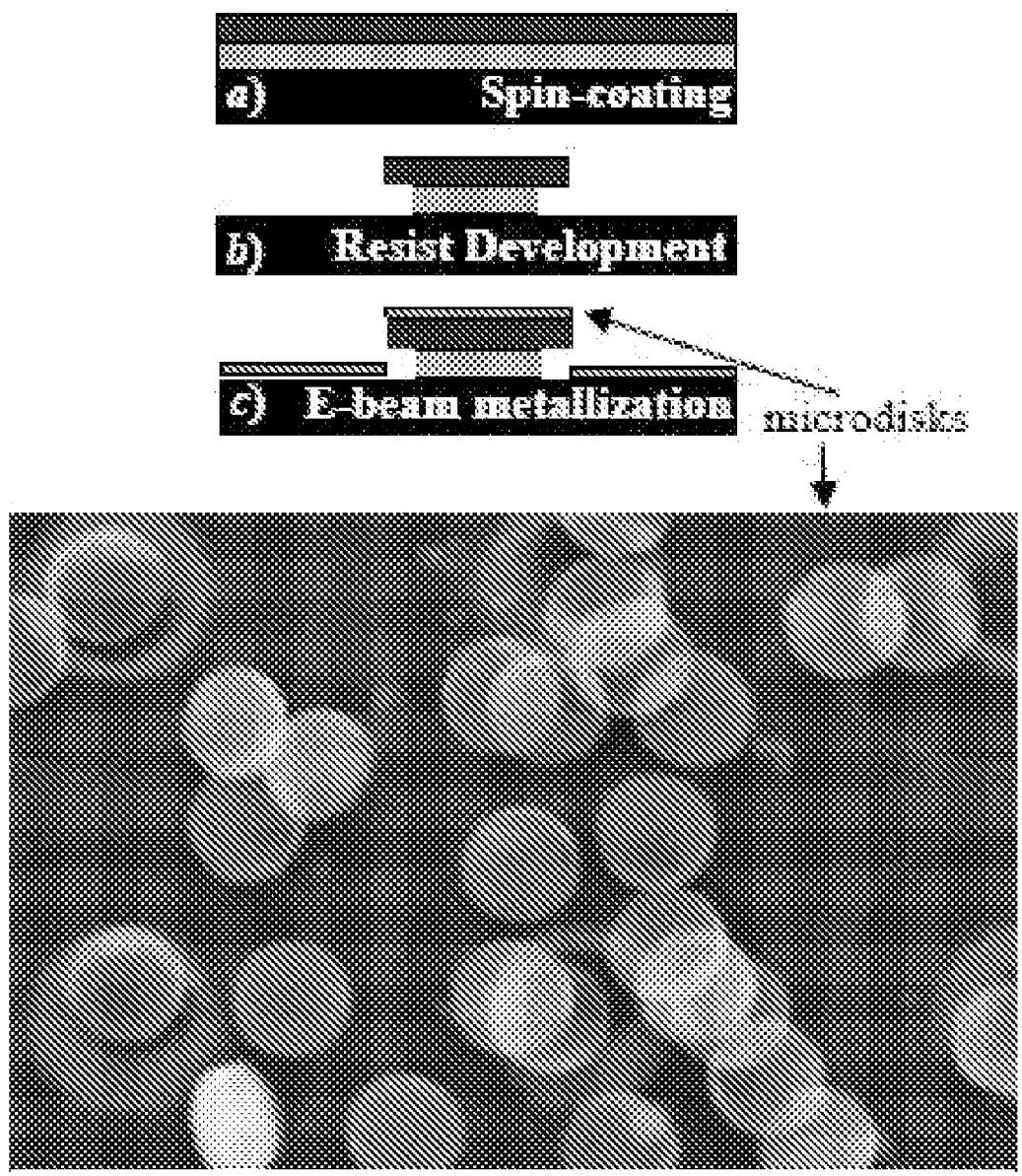
FIG. 2 shows the microfabrication steps to make ferromagnetic microdisks (top), and an electron micrograph of fabricated microdisks (bottom).

FIG. 2 shows a method of manufacturing ferromagnetic microdisks. Ferromagnetic microdisks are made by photolithography methods well known in the art, wherein ferromagnetic materials such as permalloy undergo spin-coating, resist development, and E-beam metallization. The unique resonance frequency is determined, and can be altered by, changing the geometry of the microdisk, including changing the diameter and thickness of the microdisk. The manufacture and resonance frequency characteristics of ferromagnetic microdisks have been described in the art (see Novosad, et al., Magnetic Vortex Resonance in Patterned Ferromagnetic Dots, *Physical Review*, B72, 024455-1-5 (2005); see also Novosad, et al., Ferromagnetic Microdisks: Novel magnetic Particles for Biomedical Applications, NSTI-Nanotech, vol. 1:308-311 (2005) (the entire disclosures of which are hereby incorporated by reference).

Example 3

Permalloy ferromagnetic microdisks are manufactured in a variety of thicknesses and diameters by methods known in the art. Three microdisk geometries are made to demonstrate the effect of variable geometry on resonance frequency:

| Diameter (μm) | Thickness (nm) | Frequency (mHz) |
|---|---|---|
| 2.0 | 20 | 83 |
| 2.2 | 40 | 162 |
| 1.1 | 40 | 272 |

Figure 3:
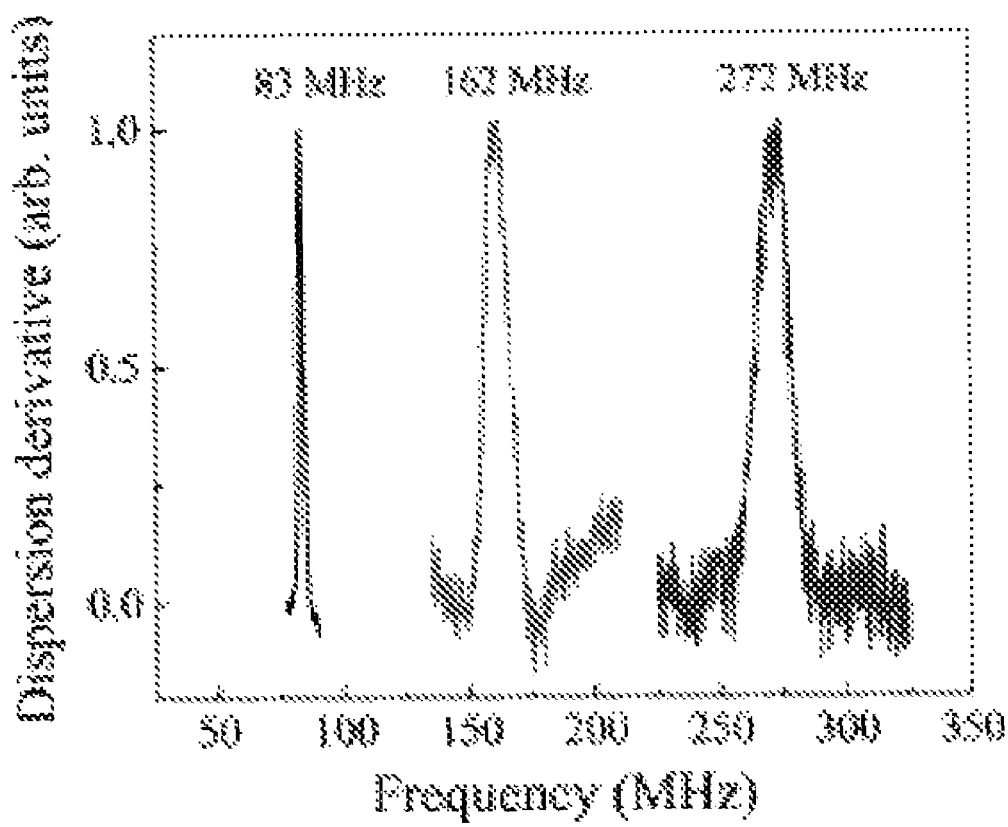
FIG. 3 shows the resonance frequency characteristics exhibited by ferromagnetic microdisks having three different geometries (L=thickness, R=radius).

FIG. 3 shows the data for these microdisks. The resonances at 83, 162, and 172 mHz, respectively, are in agreement with the eigenfrequencies of the collective spin excitations simulated micromagnetically and analytically. The number of frequency sweeps average 320, 160, and 640 respectively.

The resonance frequency of each ferromagnetic microdisk can be detected, thereby demonstrating the presence of one or more microdisks having that unique resonance frequency. In this manner, a user can bioconjugate a molecular probe to a ferromagnetic microdisk of known unique resonance frequency. The molecular probe/ferromagnetic disk is a "complex" that can be used to target, locate, identify, and quantify bioanalytes of interest that are complementary, or bind to, the molecular probe. Molecular probes, methods of bioconjugation (molecular probe to ferromagnetic disk), as well as binding of ferromagnetic disk/molecular probe complex to bioanalyte of interest (for example, hybridization or chemical linking) are well known in the art and easily within the skill of a person in the art.

Conveniently, either the sample or the ferromagnetic disk/molecular probe complex(es) can be applied and bound to a solid or semi solid substrate, such as for example, glass. In this manner, manual or automated dispensers (such as for example, robots) can be used to produce "arrays" containing multiple different ferromagnetic disks, each with their own unique resonance frequency or molecular probe. Accordingly, a sample can be contact to the ferromagnetic disk array, and several different bioanalytes of interest can be evaluated in one experiment, allowing for high throughput uses. Array formats and technologies, such as robotic dispensers, array substrates, and pattern algorithms are well known in the art. Advantageously, in such array or high throughput uses, the unique resonance frequency "signal" emitted by the ferromagnetic disk/molecular probe complex does not fade or decay over time. Also, such signals are not harmful to users, as are radioisotopes. Ferromagnetic disks can be discarded without concern for radioactive contamination of the environment.

Commercial applications for the products and methods described herein include environmental toxicology and remediation, biomedicine, materials quality control, food and agricultural products monitoring, anesthetic detection, automobile oil or radiator fluid monitoring, breath alcohol analyzers, hazardous spill identification, explosives detection, fugitive emission identification, medical diagnostics, fish freshness, detection and classification of bacteria and microorganisms both in vitro and in vivo for biomedical uses and medical diagnostic uses, monitoring heavy industrial manufacturing, ambient air monitoring, worker protection, emissions control, product quality testing, leak detection and identification, oil/gas petrochemical applications, combustible gas detection, $H_2S$ monitoring, hazardous leak detection and identification, emergency response and law enforcement applications, illegal substance detection and identification, arson investigation, enclosed space surveying, utility and power applications, emissions monitoring, transformer fault detection, food/beverage/agriculture applications, freshness detection, fruit ripening control, fermentation process monitoring and control applications, flavor composition and identification, product quality and identification, refrigerant and fumigant detection, cosmetic/perfume/fragrance formulation, product quality testing, personal identification, chemical/plastics/pharmaceutical applications, leak detection, solvent recovery effectiveness, perimeter monitoring, product quality testing, hazardous waste site applications, fugitive emission detection and identification, leak detection and identification, perimeter monitoring, transportation, hazardous spill monitoring, refueling operations, shipping container inspection, diesel/gasoline/aviation fuel identification, building/residential natural gas detection, formaldehyde detection, smoke detection, fire detection, automatic ventilation control applications (cooking, smoking, etc.), air intake monitoring, hospital/medical anesthesia & sterilization gas detection, infectious disease detection and breath applications, body fluids analysis, pharmaceutical applications, drug discovery, tele-surgery, and the like.

This application discloses several numerical range limitations that support any range within the disclosed numerical ranges even though a precise range limitation is not stated verbatim in the specification because the embodiments of the invention could be practiced throughout the disclosed numerical ranges. Finally, the entire disclosure of the patents and publications referred in this application, if any, are hereby incorporated herein in entirety by reference.

The invention claimed is:

1. A ferromagnetic microdisk comprising:
   a ferromagnetic material;
   a unique resonance frequency determined by a geometry comprising a diameter and a thickness of the microdisk; and
   a molecular probe attached to the ferromagnetic microdisk,
   wherein the unique resonance frequency is from about 20 megahertz to about 400 megahertz.

2. The ferromagnetic microdisk of claim 1 wherein the ferromagnetic material is selected from the group consisting of permalloy, CoNiFe, CoFe, CoFeCu, CoZrTa, and other ferromagnetic metals or alloys.

3. The ferromagnetic microdisk of claim 1 wherein the ferromagnetic material is permalloy.

4. The ferromagnetic microdisk of claim 1 wherein the geometry of the microdisk is determined by photolithography.

5. The ferromagnetic microdisk of claim 1 wherein the diameter is from about 0.5 µm to about 3.0 µm.

6. The ferromagnetic microdisk of claim 1 wherein the diameter is about 1.1 µm.

7. The ferromagnetic microdisk of claim 1 wherein the diameter is about 2.2 µm.

8. The ferromagnetic microdisk of claim 1 wherein the thickness is from about 10 nanometers to about 50 nanometers.

9. The ferromagnetic microdisk of claim 1 wherein the thickness is about 20 nanometers.

10. The ferromagnetic microdisk of claim 1 wherein the thickness is about 40 nanometers.

11. The ferromagnetic microdisk of claim 1 wherein the unique resonance frequency is about 83 megahertz.

12. The ferromagnetic microdisk of claim 1 wherein the unique resonance frequency is about 162 megahertz.

13. The ferromagnetic microdisk of claim 1 wherein the unique resonance frequency is about 272 megahertz.

14. The ferromagnetic microdisk of claim 1 further comprising a molecular probe attached to the surface of the ferromagnetic microdisk.

15. The ferromagnetic microdisk of claim 14 wherein the molecular probe is selected from the group consisting of DNA, RNA, antibody, and protein.

16. The ferromagnetic microdisk of claim 14 wherein the molecular probe comprises protein.

17. A kit comprising:
    one or more ferromagnetic microdisks; and
    one or more molecular probes,
    wherein the ferromagnetic microdisks comprise a ferromagnetic material and a unique resonance frequency determined by a geometry comprising a diameter and a thickness of the microdisk,
    wherein the unique resonance frequency is from about 20 megahertz to about 400 megahertz.

18. The kit of claim 17 wherein the ferromagnetic microdisk comprises a material selected from the group consisting of permalloy, CoNiFe, CoFe, CoFeCu, CoZrTa, and other ferromagnetic metals or alloys.

19. The kit of claim 17 wherein the ferromagnetic microdisk comprises permalloy film.

20. The kit of claim 17 wherein the molecular probe is selected from the group consisting of DNA, RNA, and protein.

21. The kit of claim 17 wherein the molecular probe comprises protein.

22. The kit of claim 17 wherein the geometry of the ferromagnetic microdisk is determined by photolithography.

23. The kit of claim 17 wherein the diameter of the ferromagnetic microdisk is from about 0.5 µm to about 3.0 µm.

24. The kit of claim 17 wherein the diameter of the ferromagnetic microdisk is about 1.1 µm.

25. The kit of claim 17 wherein the diameter of the ferromagnetic microdisk is about 2.2 µm.

26. The kit of claim 17 wherein the thickness of the ferromagnetic microdisk is from about 10 nanometers to about 50 nanometers.

27. The kit of claim 17 wherein the thickness of the ferromagnetic microdisk is about 20 nanometers.

28. The kit of claim 17 wherein the thickness of the ferromagnetic microdisk is about 40 nanometers.

29. The kit of claim 17 wherein the unique resonance frequency of the ferromagnetic microdisk is about 83 megahertz.

30. The kit of claim 17 wherein the unique resonance frequency of the ferromagnetic microdisk is about 162 megahertz.

31. The kit of claim 17 wherein the unique resonance frequency of the ferromagnetic microdisk is about 272 megahertz.

* * * * *